United States Patent [19]

Chu

[11] Patent Number: 4,689,325
[45] Date of Patent: Aug. 25, 1987

[54] ISOXAZOLO-PYRIDO-PHENOXAZINE AND ISOTHIAZOLO-PYRIDO-PHENOXAZINE DERIVATIVES

[75] Inventor: Daniel T. Chu, Vernon Hills, Ill.

[73] Assignee: Abbott Laboratories, North Chicago, Ill.

[21] Appl. No.: 919,344

[22] Filed: Oct. 15, 1986

Related U.S. Application Data

[63] Continuation-in-part of Ser. No. 812,559, Dec. 23, 1985, abandoned.

[51] Int. Cl.$^4$ .................. A61K 31/535; C07D 498/14
[52] U.S. Cl. ..................................... 514/211; 514/218; 514/222; 514/229; 514/234; 540/544; 540/575; 544/58.6; 544/99
[58] Field of Search ............... 544/58.6, 99; 540/544, 540/575; 514/211, 218, 222, 229, 234

[56] References Cited

U.S. PATENT DOCUMENTS

| | | |
|---|---|---|
| 3,149,104 | 9/1964 | Lesher et al. ............... 260/240 |
| 4,017,622 | 4/1977 | Minami ......................... 424/250 |
| 4,146,719 | 4/1979 | Irikura ........................... 544/363 |
| 4,284,629 | 8/1981 | Grohe et al. ................ 546/318 X |
| 4,382,892 | 5/1983 | Hayakawa et al. .......... 544/73 X |
| 4,415,572 | 11/1983 | Tominaga et al. .......... 544/363 X |
| 4,429,127 | 1/1984 | Irikura et al. ................ 544/363 |
| 4,439,436 | 3/1984 | Wentland et al. ........... 546/90 X |
| 4,443,447 | 4/1984 | Gerster et al. ............... 544/105 X |
| 4,473,568 | 9/1984 | Hutt, Jr. ....................... 544/101 X |
| 4,540,694 | 9/1985 | Chu ............................... 544/99 X |
| 4,542,133 | 9/1985 | Chu ............................... 544/99 X |

FOREIGN PATENT DOCUMENTS

| | | |
|---|---|---|
| 0009425 | 4/1980 | European Pat. Off. . |
| 0078362 | 7/1982 | European Pat. Off. . |
| 2362553 | 12/1973 | Fed. Rep. of Germany . |
| 2338325 | 2/1974 | Fed. Rep. of Germany . |
| 2341146 | 2/1974 | Fed. Rep. of Germany . |
| 3142854 | 5/1983 | Fed. Rep. of Germany . |
| 5128764 | 8/1981 | Japan . |
| 1147336 | 4/1969 | United Kingdom . |
| 2034698 | 11/1972 | United Kingdom . |

OTHER PUBLICATIONS

Sato et al, "In Vitro and In Vivo Activity of DL-8280, a New Oxazine Derivative", *Antimicrobial Agents and Chemotherapy*, vol. 22, No. 4, pp. 548–553, Oct. 1982.
Koga et al., "SAR of Substituted Quinoline-3-Carboxylic Acids" *Journal of Medicinal Chemistry*, 1980, vol. 23, No. 12, p. 1358.

*Primary Examiner*—Richard L. Raymond
*Attorney, Agent, or Firm*—Martin L. Katz; Robert W. Stevenson

[57] ABSTRACT

This invention relates to novel isoxazolo-pyridophenoxazine and isothiazolo-pyridophenoxazine derivatives having antibacterial properties and compositions containing methods of treating mammalian patients with these new derivatives.

12 Claims, No Drawings

ISOXAZOLO-PYRIDO-PHENOXAZINE AND ISOTHIAZOLO-PYRIDO-PHENOXAZINE DERIVATIVES

This application is a continuation-in-part of application Ser. No. 812,559 filed Dec. 23, 1985 entitled Isoxazolo-Pyrido-Phenoxazine and Isothiazolo-Pyrido Phenoxazine Derivatives, now abandoned.

This invention related to novel antibacterial agents and, more particularly, to phenoxazine derivatives having the formula:

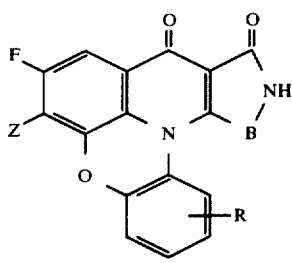

which may exist in its tautomer form (II).

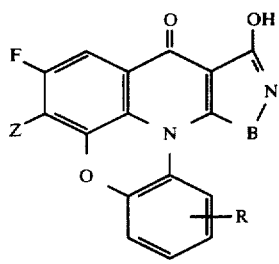

wherein B is oxygen or sulfur; and R is one or more of a hydrogen, halogen, $C_1$ to $C_4$ alkyl including halo- and hydroxy-substituted derivatives thereof, carboxyl, a group having the formula —Y—$R_1$ wherein —Y— is —O— or —S— and $R_1$ is hydrogen or $C_1$ to $C_4$ alkyl, and an amine having the formula:

wherein $R_2$ and $R_3$ are each independently a hydrogen or $C_1$ to $C_4$ alkyl. R may also be methylenedioxy group bonded to two adjacent carbon atoms of the aromatic ring.

Z is an amino group having the formula:

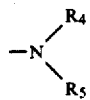

wherein $R_4$ is hydrogen, $C_1$ to $C_4$ alkyl or hydroxy-substituted $C_1$ to $C_4$ alkyl, and $R_5$ is alkyl or hydroxy-substituted $C_1$ to $C_4$ alkyl, an amino group, mono-($C_1$-$C_4$) alkylamino or di-($C_1$-$C_4$) alkylamino.

Alternatively, Z can be an aliphatic heterocyclic ring containing 5 to 7 atoms, and preferably 5 to 6 atoms as well as substituted derivatives thereof. The aliphatic heterocyclic rings preferably contain 1 to 2 hetero atoms which are selected from the group consisting of S, O, N and combinations thereof, with the remaining carbon atoms. In accordance with the invention, the aliphatic heterocyclic ring has the formula:

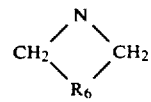

wherein $R_6$ is selected from the group of formula (—$CH_2$)$_{11}$— wherein n is 2 or 3 and a group of the formula —($CH_2$)$_n$—$R_7$—$CH_2$— wherein n is 1 or 2 and $R_7$ is selected from the group consisting of —S—, —O— and —N—. Also included are substituted derivatives of the above-noted aliphatic heterocyclic rings wherein the substituent is one or more of a $C_1$ to $C_4$ alkyl group, hydroxy-substituted $C_1$ to $C_4$ alkyl, amino-substituted $C_1$ to $C_4$ alkyl, hydroxy, halogen, phenyl, halophenyl, alkanoylamido containing 1 to 4 carbon atoms, an amine group having the formula:

wherein $R_8$ and $R_9$ are each independently selected from the group consisting of hydrogen, $C_1$ to $C_4$ alkyl.

Illustrative of such heterocyclic groups are piperazinyl groups, piperidinyl groups, pyrrolidinyl groups, morpholino groups, thiomorpholino groups and homopiperazinyl groups (i.e., hexahydro-1-H-1,4-diazepinyl).

As used herein, the term "halogen" refers to chloro, bromo, fluoro and iodo groups, while the term "$C_1$ to $C_4$ alkyl" refers to lower alkyl groups including methyl, ethyl, propyl, isopropyl, butyl, etc.

Carboxyl refers to the —COOH group. Methylenedioxy refers to —O—$CH_2$—O—group.

The term "amino" refers to —$NH_2$.

The term "alkanoylamido" refers to a substituent of the formula $R_{10}$CN— wherein $R_{10}$ is $C_1$ to $C_3$ alkyl, and includes but is not limited to acetylamino.

The preferred compound of the invention are those having the formula:

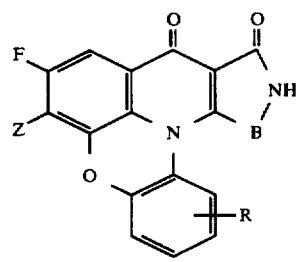

where B is oxygen or sulfur; and R is one or more of halogen, methylenedioxy and and Z is piperazinyl or substituted piperazinyl, aminopyrrolidinyl, substituted pyrrolidinyl or substituted aminopyrrolidinyl, as described above.

The chiral centers of the compounds of the invention may have either the "R" or "S" configuration.

Representative of such preferred compounds, wherein B is oxygen, are 6-(1-piperazinyl)-7-fluoro-10,11-dihydro-9H-isoxazolo[4',5':5,6]pyrido[1,2,3-mn]phenoxazine-9,10-dione, 6-(4-methyl-1-piperazinyl)-7-fluoro-10,11-dihydro-9H-isoxazolo[4',5':5,6-]pyrido[1,2,3-mn]phenoxazine-9,10-dione, 6-(3-N-ethyl aminomethyl pyrrolidin-1-yl)-7-fluoro-10,11-dihydro-9H-isoxazolo[4',5':5,6]pyrido[1,2,3-mn]phenoxazine-9,10-dione, 6-(3-amino-1-pyrrolidinyl)-7-fluoro-10,11-dihydro-9H-isoxazolo[4',5':5,6]pyrido[1,2,3-mn]phenoxazine-9,10-dione, 6-(3-methyl-1-piperazinyl)-3,7-difluoro-10,11-dihydro-9H-isoxazolo[4',5':5,6-]pyrido[1,2,3-mn]phenoxazine-9,10-dione, 6-(3-amino-4-methyl-1-pyrrolidinyl)-3,7-difluoro-10,11-dihydro-9H-isoxazolo[4',5':5,6]pyrido[1,2,3-mn]phenoxazine-9,10-dione, 3,7-difluoro-6-(1-piperazinyl)-10,11-dihydro-9H-isoxazolo[4',5':5,6]pyrido[1,2,3-mn]phenoxazine-9,10-dione, 3,7-difluoro-6-(4-methyl-1-piperazinyl)-10,11-dihydro-9H-isoxazolo[4',5':5,6]pyrido[1,2,3-mn]phenoxazine-9,10-dione, 3,7-difluoro-6-(3-amino-1-pyrrolidinyl)-10,11-dihydro-9H-isoxazolo[4',5':5,6-]pyrido[1,2,3-mn]phenoxazine-9,10-dione, 6-(3-aminomethyl-4-chloro-1-pyrrolidinyl)-3,7-difluoro-10,11-dihydro-9H-isoxazolo[4',5':5,6]pyrido[1,2,3-mn]phenoxazine-9,10-dione, 1,3,7-trifluoro-6-(1-piperazinyl)-10,11-dihydro-9H-isoxazolo[4',5':5,6-]pyrido[1,2,3-mn]phenoxazine-9,10-dione, 1,3,7-trifluoro-6-(4-methyl-1-piperazinyl)-10,11-dihydro-9H-isoxazolo[4',5':5,6]pyrido[1,2,3-mn]phenoxazine-9,10-dione, 1,3,5-trifluoro-6-(3-amino-1-pyrrolidinyl)-10,11-dihydro-9H-isoxazolo[4',5':5,6]pyrido[1,2,3-mn]phenoxazine-9,10-dione.

Representative of such preferred compounds, wherein B is sulfur, are 6-(1-piperazinyl)-7-fluoro-10,11-dihydro-9H-isothiazolo[4',5':5,6]pyrido[1,2,3-mn]phenoxazine-9,10-dione, 6-(4-methyl-1-piperazinyl)-7-fluoro-10,11-dihydro-9H-isothiazolo[4',5':5,6-]pyrido[1,2,3-mn]phenoxazine-9,10-dione, 6-(2-methyl-4-amino-pyrrolidin-1-yl)-7-fluoro-10,11-dihydro-9H-isothiazolo[4',5':5,6]pyrido[1,2,3-mn]phenoxazine-9,10,dione, 6-(3-amino-1-pyrrolidinyl)-7-fluoro-10,11-dihydro-9H-isothiazolo[4',5':5,6]pyrido[1,2,3-mn]phenoxazine-9,10-dione, 6-(3-methyl-1-piperazinyl)-3,7-difluoro-10,11-dihydro-9H-isothiazolo[4',5':5,6-]pyrido[1,2,3-mn]phenoxazine-9,10-dione, 6-(3-amino-4-methyl-1-pyrrolidinyl)-3,7-difluoro-10,11-dihydro-9H-isothiazolo[4',5':5,6]pryido[1,2,3-mn]phenoxazine-9,10-dione, 3,7-difluoro-6-(1-piperazinyl)-10,11-dihydro-9H-isothiazolo[4',5':5,6]pyrido[1,2,3-mn]phenoxazine-9,10-dione, 3,7-difluoro-6-(4-methyl-1-piperazinyl)-10,11-dihydro-9H-isothiazolo[4',5':5,6]pyrido[1,2,3-mn]phenoxazine-9,10-dione, 3,7-difluoro-6-(3-amino-1-pyrrolidinyl)-10,11-dihydro-9H-isothiazolo[4',5':5,6-]pyrido[1,2,3-mn]phenoxazine-9,10-dione, 6-(3-aminomethyl-4-chloro-1-pyrrolidinyl)-3,7-difluoro-10,11-dihydro-9H-isothiazolo[4',5':5,6]pyrido[1,2,3-mn]phenoxazine-9,10-dione, 1,3,7-trifluoro-6-(1-piperazinyl)-10,11-dihydro-9H-isothiazolo[4',5':5,6-]pyrido[1,2,3-mn]phenoxazine-9,10-dione, 1,3,7-trifluoro-6-(4-methyl-1-piperazinyl)-10,11-dihydro-9H-isothiazolo[4',5':5,6]pyrido[1,2,3-mn]phenoxazine-9,10-dione, 1,3,5-trifluoro-6-(3-amino-1-pyrrolidinyl)-10,11-dihydro-9H-isothiazolo[4',5':5,6]pyrido[1,2,3-mn]phenoxazine-9,10-dione.

Also included within the scope of the present invention are pharmaceutically acceptable salts of the foregoing compounds. As used herein, the term "pharmaceutically acceptable salts" refers to non-toxic acid addition salts and alkaline earth metal salts of the compounds of the invention. The salts can be prepared in situ during the final isolation and purification of the compounds of the invention, or separately by reacting the free base or acid functions with a suitable organic acid or base. Representative acid addition salts include the hydrochloride, hydrobromide, sulphate, bisulphate, acetate, oxalate, valerate, oleate, palmitate, stearate, laurate, borate, benzoate, lactate, phosphate, tosylate, mesylate, citrate, maleate, fumarate, succinate, tartrate glucoheptonate, lactobionate, lauryl sulfate salts and the like. Representative alkali or alkaline earth metal salts include the sodium, calcium, potassium and magnesium salts, etc. It has been found that the compounds of the present invention possess antibacterial activity against a wide spectrum of gram positive and gram negative bacteria, as well as enterobacteria. The compounds of the invention are therefor useful in the antibiotic treatment of susceptible bacterial infections in both humans and animals. In addition, the compounds, by reason of their in vitro activity, may be used in scrub solutions for surface inhibition of bacterial growth.

Susceptible organisms generally include those gram positive and gram negative, aerobic and anaerobic organisms whose growth can be inhibited by the compounds of the invention such as Staphlococcus, Lactobacillus, Streptococcus, Sarcina, Escherichia, Enterobacter, Klebseilla, Pseudomonas, Acinetobacter, Proteus, Citrobacter, Nisseria, Baccillus, Bacteroides, Peptococcus, Clostridium, Salmonella, Shigella, Serratia, Haemophilus, Brucella, and other organisms.

The compounds of the invention may also be formulated into compositions together with pharmaceutically acceptable carriers for parenteral injection, for oral administration in solid or liquid form, for rectal administration, and the like.

Compositions according to the invention for parenteral injection may comprise pharmaceutically acceptable sterile aqueous or nonaqueous solutions, suspensions or emulsions. Examples of suitable nonaqueous carriers, diluents, solvents or vehicles include propylene glycol, polyethylene glycol, vegetable oils, such as olive oil, and injectable organic esters such as ethyl oleate. Such compositions may also contain adjuvants such as preserving, wetting, emulsifying, and dispersing agents. They may be sterilized, for example, by filtration through a bacteria-retaining filter, or by incorporating sterilizing agents into the compositions. They can also be manufactured in the form of sterile solid compositions which can be dissolved in sterile water, or some other sterile injectable medium immediately before use.

Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups and elixers containing inert diluents commonly used in the art, such as water. Besides such inert diluents, compositions can also include adjuvants, such as wetting agents, emulsifying and suspending agents, and sweetening, flavoring and perfuming agents.

Compositions for rectal adminstration are preferably suppositories which may contain, in addition to the active substance, excipients such as cocoa butter or a suppository wax.

Actual dosage levels of active ingredient in the compositions of the invention may be varied so as to obtain an amount of active ingredient effective to achieve antibacterial activity in accordance with the desired method of adminstration. The selected dosage level therefore depends upon the nature of the active compound administered, the route of administration, the desired duration of treatment and other factors. Generally, daily dosage levels of the compounds of the invention of about 0.1 to about 750, more preferably about 0.25 to about 500 and most preferably about 0.5 to about 300 mg. of active ingredient per kg. of body weight are effective when administered orally to a mammalian patient suffering from an infection caused by a susceptible organism. If desired, the daily dose may be divided into multiple doses for administration, e.g., two to four time per day.

Compounds wherein B is oxygen according to this invention can be prepared by the following reaction scheme in which Z and R are as described above, and $R_{11}$ is $C_1$ to $C_4$ alkyl group.

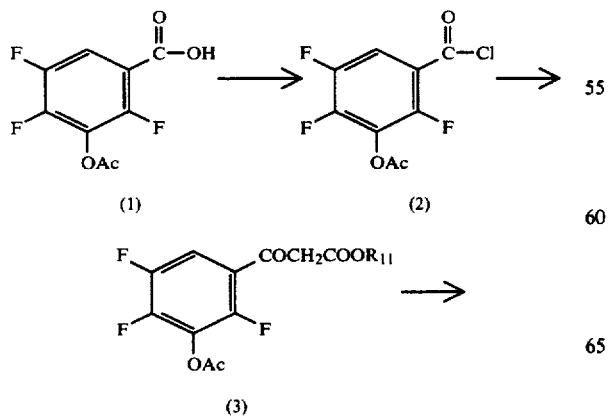

-continued

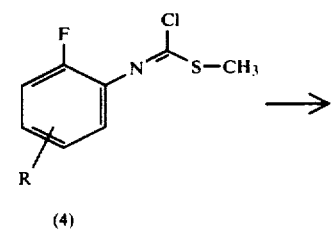

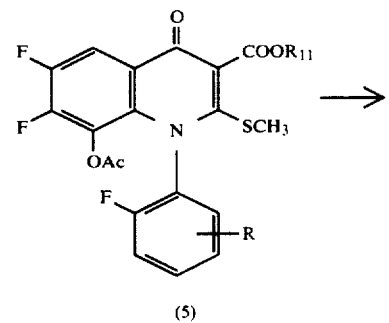

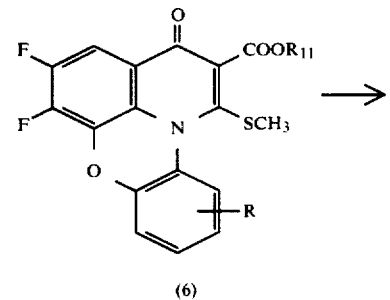

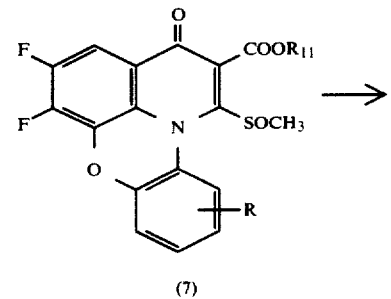

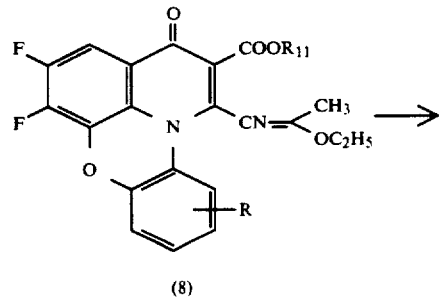

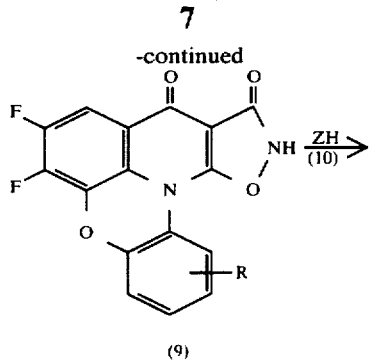

(9)

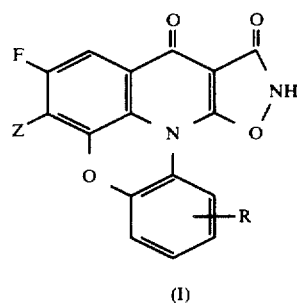

(I)

In accordance with the above scheme, the substituted benzoic acid (1) can be converted to its acid chloride (2) by treatment with thionyl chloride. Displacement of the acid chloride (2) with malonic acid half ester in the presence of n-butyl lithium yields the beta-ketoester (3). Treatment of the beta-keto ester (3) with sodium hydride in non-aprotic solvent, preferably tetrahydrofuran with methyl N-substituted iminochlorothioformate (4) at room temperature or suitable elevated temperature as desired yields the 1,4-dihydro-4-oxo-quinoline-3-carboxylic acid ester (5).

Treatment of this ester (5) with dilute acid in aqueous acetonitrile for a period of time gives a phenol then reacted with sodium hydride to give the phenoxazine derivative (6).

Oxidation of this derivative (6) with metachlorperbenzoic acid yields the sulfoxide (7). The reaction may be conducted at room temperature or elevated temperature in the presence of non-polar solvent such as methylene chloride or chloroform.

Reaction of the sulfoxide (7) with ethyl acetohydroxamate in the presence of a strong base such as sodium hydride or potassium t-butoxide in aprotic or non-aprotic solvent such as tetrahydrofuran at a temperature from 0° C. to elevated temperature yields the hydroxomate (8). Treatment of hydroxamate (8) with trifluoroacetic acid or dilute hydrochloric acid at room temperature or with perchloric acid at 0° C. for a short time yields the free hydroxylamine derivative which is then reacted with sodium bicarbonate in aqueous tetrahydrofuran at room temperature or suitable elevated temperature to yield the 6,7-difluoro-10,11-dihydro-9H-isoxazolo[4',5':5,6]pyrido[1,2,3-mn]substituted phenoxazine-9,10-dione derivative (9).

Displacement of the 6-halogen of (9) with an amine (10) yields the 6-substituted amino-isoxazolo-pyridophenoxazine (I). The reaction may be conducted at a temperature from 20° C. to 130° C. in the presence of a suitable organic polar or non-polar solvent such as pyridine, methylene chloride, chloroform, tetra-hydrofuran, 1-methyl-2-pyrrolidinone, dimethyl formamide or dimethyl-sulfoxide. It is desirable to carry out the reaction in the presence of an acid-acceptor such as triethylamine, potassium carbonate and the like at a molar ratio of 1.0 to 1.2 moles of the acid-acceptor per mole of the compound of the formula (9). The amine (10) can also be used as acid acceptor in which 2 or more molar excess of this reagent is used.

Alternatively, compounds according to this invention wherein B is oxygen, can also be prepared by the following scheme.

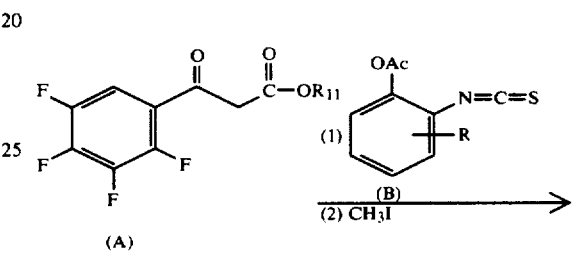

(A)

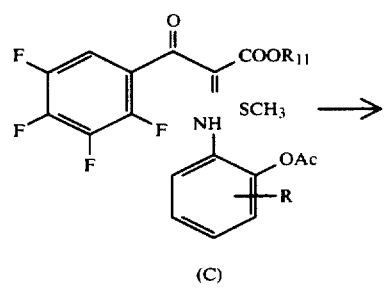

(C)

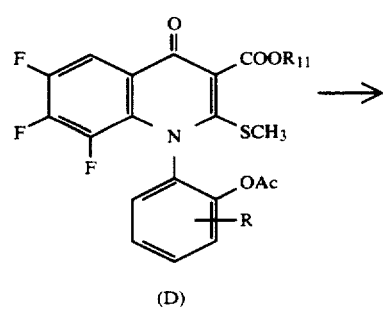

(D)

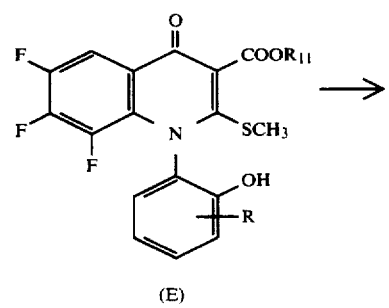

(E)

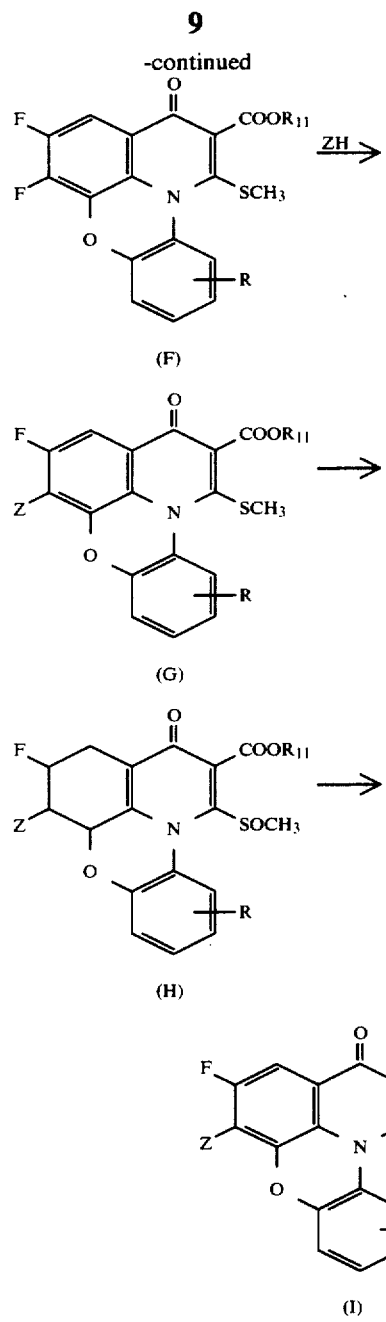

(F)

(G)

(H)

(I)

In accordance with the foregoing reaction scheme, the alkyl 2-(2,3,4,5-tetrafluoro)benzoyl acetate (A) can be converted to the anilino compound (C) by treatment of the acetate (A) with sodium hydride in non-aprotic solvent, preferably tetrahydrofuran and the substituted phenyl isothiocyanate (B) and then reacting the intermediate in situ with methyl iodide. The reaction can be carried out at room temperature or elevated temperature as desired. Treatment of this anilino compound (C) with sodium hydride in THF or dimethylformanide at room temperature or elevated temperature yields the 1,4-dihydro-4-oxo-quinoline-3-carboxylic acid ester (D). Reaction of this ester (D) with dilute acid in aqueous acetonitrile or other suitable solvent for a period of time gives the phenol (E). Treatment of this alcohol (E) with sodium hydride in non-aprotic solvent or other strong base such as sodium hydroxide, or lithium dialkylamides such as lithium di-isopropylamide, lithium bistrimethylsilylamide yields the phenoxazine derivative (F). Reaction of the phenoxazine (F) with an amine (ZH) yields the amino substituted derivative (G). The reaction may be conducted at a temperature from 20° C. to 130° C. in the presence of a suitable organic polar or non-polar solvent such as pyridine, methylene chloride, chloroform, tetrahydrofuran, 1-methyl-2-pyrrolidinone, dimethylformamide or dimethylsulfoxide. Oxidation of compound (G) with metachloroperbenzoic acid or other peracid in methylene chloride or other organic solvent or in an aqueous or non-aqueous acidic medium yields the sulfoxide (H). Treatment of this sulfoxide (H) with N-hydroxyurea in an aprotic or non-aprotic solvent such as ethanol, methanol, tertbutyl alcohol, tetrahydrofuran and dimethylformamide, in the presence of a base such as DBU, DBN, sodium hydride, and potassium t-butoxide gives the 6-(substituted amino)-7-fluoro-10,11-dihydro-9-H-isoxazolo[4',5':5,6-]pyrido[1,2,3-mn]substituted phenoxazine-9,10-dione (I). The reaction may be conducted at room temperature or suitable elevated temperature.

Compounds wherein B is sulfur can be prepared by the following reaction scheme in which Z and R are as described above, and $R_{11}$ is $C_1$ to $C_4$ alkyl group.

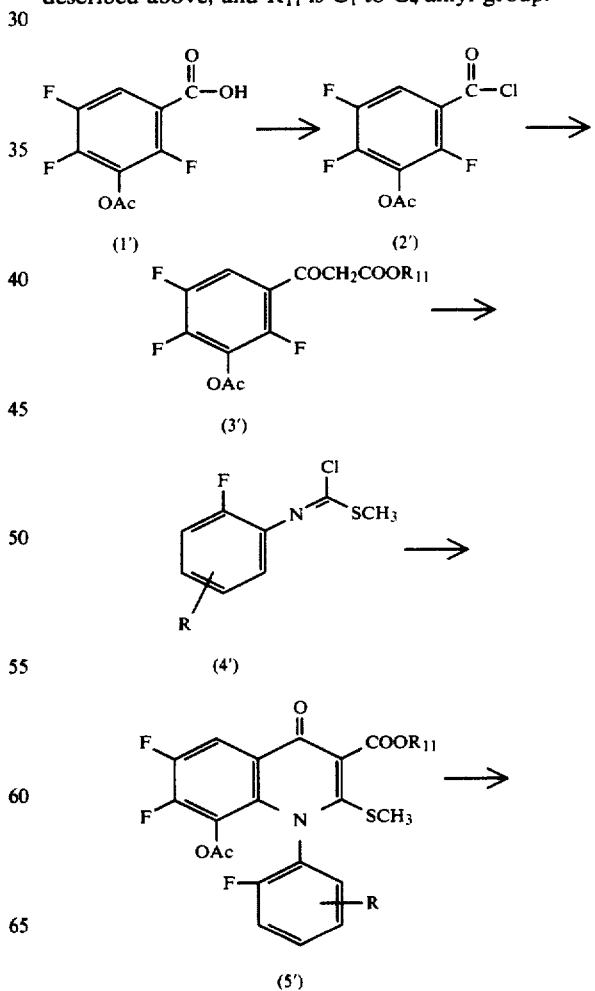

(1')

(2')

(3')

(4')

(5')

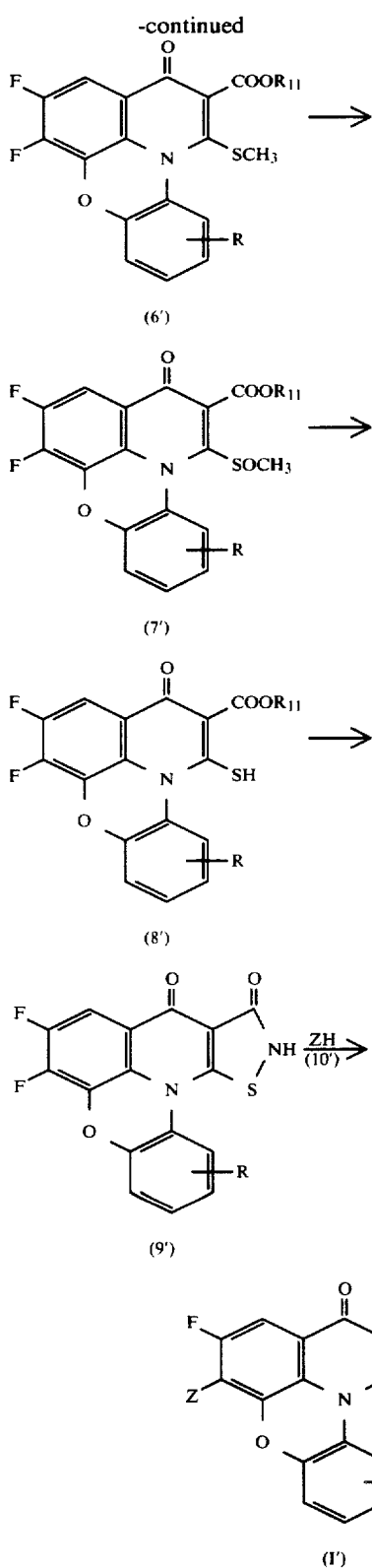

(3'). Treatment of the beta-keto ester (3') with sodium hydride in non-aprotic solvent, preferably tetrahydrofuran with methyl N-substituted iminochlorothioformate (4') at room temperature or suitable elevated temperature as desired yields the 1,4-dihydro-4-oxo-quinoline-3-carboxylic acid ester (5').

Treatment of this ester (5') with dilute acid in aqueous acetonitrile for a period of time gives a phenol which is then reacted with sodium hydride to give the phenoxazine derivative (6').

Oxidation of this derivative (6') with metachlorperbenzoic acid yields the sulfoxide (7'). The reaction may be conducted at room temperature or elevated temperature in the presence of non-polar solvent such as methylene chloride or chloroform.

Reaction of (7') with sodium hydrosulfide in an aprotic solvent, preferably aqueous tetrahydrofuran, at room or elevated temperature yields the 4-mercapto-derivative (8'). Treatment of (8') with hydroxylamine-O-sulfonic acid in the presence of a base, preferably sodium bicarbonate in aprotic solvent, preferably aqueous tetrahydrofuran yields the 6,7-difluoro-10,11-dihydro-9H-isothiazolo[4',5':5,6]pyrido[1,2,3-mn]substituted phenoxazine-9,10-dione derivative (9').

Displacement of the 6-halogen of (9') with an amine (10') yields the 6-substituted amino-isothiazolo-pyrido-phenoxazine (I'). The reaction may be conducted at a temperature from 20° C. to 130° C. in the presence of a suitable organic polar or non-polar solvent such as pyridine, methylene chloride, chloroform, tetra-hydrofuran, 1-methyl-2-pyrrolidinone, dimethyl formamide or dimethyl-sulfoxide. It is desirable to carry out the reaction in the presence of an acid-acceptor such as triethylamine, potassium carbonate and the like at a molar ratio of 1.0 to 1.2 moles of the acid-acceptor per mole of the compound of the formula (9). The amine (10) can also be used as acid acceptor in which 2 or more molar excess of this reagent is used.

Alternatively, compounds according to this invention wherein B is sulfur can also be prepared by the following scheme using compound (G) described before as starting material.

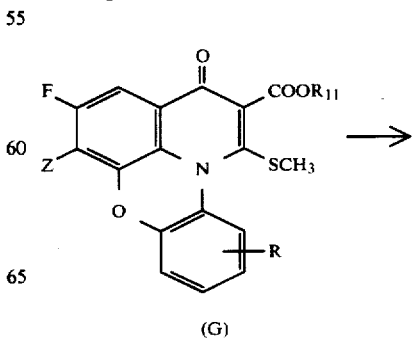

In accordance with the above scheme, the substituted benzoic acid (1') can be converted to its acid chloride (2') by treatment with thionyl chloride. Displacement of the acid chloride (2') with malonic acid half ester in the presence of n-butyl lithium yields the beta-ketoester

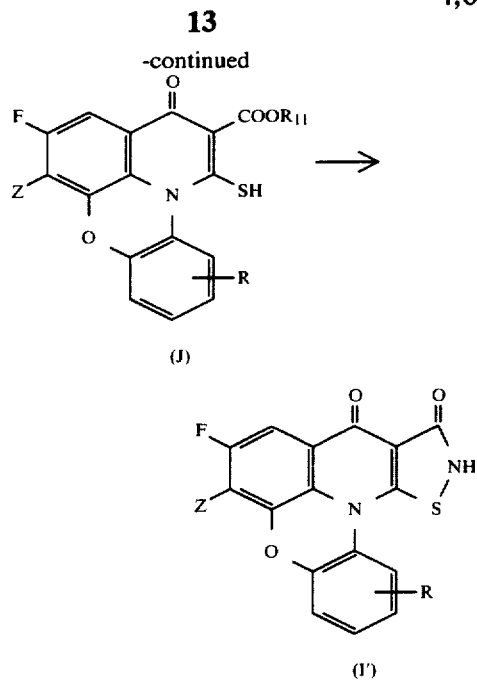

In accordance with the above scheme, treatment of the compound (G) with sodium hydrosulfide in an aprotic solvent, preferably aqueous tetrahydrofuran, at room or elevated temperature yields the mercapto-derivative (J). Reaction of compound (J) with hydroxylamine-O-sulfonic acid in the presence of a base, preferably sodium bicarbonate in an aprotic solvent preferably aqueous tetrahydrofuran yields the 6-substituted amino-7-fluoro-10,11-dihydro-9H-isothiazolo[4′,5′:5,6-]pyrido[1,2,3-mn]substituted phenoxazine-9,10-dione (I′). The reaction may be conducted at room-temperature or suitable elevated temperature.

The foregoing may be better understood from the following examples, which are presented for purposes of illustration and are not intended to limit the scope of the inventive concepts. As used in the following examples, the references to compounds, such as (1), (2), (3) or (1′), (2′), (3′), (A), (B), (C), etc., and to substituents, such as R, R$_7$, etc., refer to the corresponding compounds and substituents in the foregoing reaction schemes and in formulae I and I′. Formulae I and I′ each represent compounds of structure I on page 1 of this specification.

EXAMPLE 1

6-(4-methyl-1-piperazinyl)-7-fluoro-10,11-dihydro-9H-isoxazolo[4′,5′:5,6]pyrido[1,2,3-mn]phenoxazine-9,10-dione (a) A mixture of 1.17 g of 2,4,5-trifluoro-3-acetyloxybenzoic acid (1) and thionyl chloride (10 ml) and 1 drop of dimethylformamide is heated at refluxing temperature for 4 hours. The solution is evaporated to dryness to give the acid chloride (2). This acid chloride, dissolved in 10 ml of tetrahydrofuran (THF) is added slowly to a solution of 1.32 g of ethylmalonate monoester in 25 ml of THF solution containing 9.09 ml of 2.2 molar solution of n-butyl lithium in hexane at −60° C. It is allowed to stir at −55° C. to −60° C. for 1 hour. The solution is allowed to warm up to room temperature and then acidified with 20 ml of 1N hydrochloric acid and extracted with ether. The ether extract is washed with saturated NaHCO$_3$ and then water, and dried to yield 1.29 g of the ketoester (3) (R$_{11}$=C$_2$H$_5$).

(b) 800 mg of a 60% sodium hydride-in-oil suspension is slowly added to a solution of 2.03 g methyl N-(2-fluorophenyl)iminochlorothioformate (4) (R=H) and 4.34 g ketoester (3) (R$_{11}$=C$_2$H$_5$). The mixture is then heated at reflux for 24 hours. It is then cooled and evaporated under reduced pressure to dryness. The residue is dissolved in methylene chloride and washed with saturated sodium chloride solution. Organic layer is separated and dried over magnesium sulfate. The product is purified through silica gel column yielding the 1,4-dihydro-4-oxo-quinoline-3-carboxylate (5) (R$_{11}$=C$_2$H$_5$, R=H).

(c) To a solution of 2.75 g of the preceding compound (5) (R$_{11}$=C$_2$H$_5$, R=H) in 30 ml acetonitrile is added in 10 ml 2N hydrochloride acid solution. The mixture is stirred for 24 hours at room temperature. The mixture is then evaporated to dryness and redissolved in THF. 200 mg of sodium hydride is added. After heating for 24 hours at 50° C. the reaction mixture is then evaporated under reduced pressure to dryness. The residue is dissolved in methylene chloride and washed with water. The organic solvent is separated and dried and evaporated to dryness. After purification, it yields the phenoxazine derivative (6) (R$_{11}$=C$_2$H$_5$, R=H).

(d) To a solution of 3.90 g of the preceding compound (6) (R$_{11}$=C$_2$H$_5$, R=H) in 100 ml methylene chloride is added in 2.18 g of 80% metachloroperbenzoic acid. After stirring at 25° C. for 7 hours, the solution is diluted with 150 ml of methylene chloride and washed with dilute sodium bicarbonate solution. The organic solvent is dried over magnesium and evaporated to dryness. 15 ml of ether is added to the residue and it crystallizes yielding, after filtration the sulfoxide (7) (R$_{11}$=C$_2$H$_5$, R=H).

(e) 0.4 g of 60% sodium hydride in oil suspension is added slowly to a solution of 4.0 g of the preceding compound (7) (R$_{11}$=C$_2$H$_5$, R=H) and 1.31 g of ethyl acetohydroxamate in 80 ml THF. After stirring at room temperature for 24 hours, the mixture is evaporated to dryness and the residue is dissolved in methylene chloride (150 ml) and washed with water. The organic portion is dried and evaporated to dryness and the residue is purified by column chromatography yielding the hydroxamate (8) (R$_{11}$=C$_2$H$_5$, R=H).

(f) To a solution of 2.3 g of the preceding hydroxamate derivative (8) (R$_{11}$=C$_2$H$_5$, R=H) in 15 ml THF is added 70% perchloric acid (3 ml) with stirring at 0° C. for 10 minutes. The mixture is then poured into ice water yielding a solid which is filtered. The solid is then dissolved in 60 ml water/THF mixture and 3.2 g sodium bicarbonate in 30 ml H$_2$O is then added. After 5 hours, the mixture is extracted with either (25 ml×2). The aqueous layer is acidified with dilute hydrochloric acid to pH 3 and the precipitate is filtered yielding 6,7-difluoro-10,11-dihydro-9H-isoxazolo[4′,5′:5,6-]pyrido[1,2,3-mn]phenoxazine-9,10-dione (9) (R=H).

(g) To a solution of 1.58 g of the preceding isoxazolopyrido-phenoxazine derivative (9) (R=H) in 30 ml pyridine is added in 2.5 ml N-methylpiperazine. It is then heated under Nitrogen atmosphere at 60° C. for 24 hours. The mixture is evaporated to dryness and is then boiled in ethanol for 5 minutes and the mixture is filtered and washed with water yielding the 6-(4-methyl-1-piperazinyl)-7-fluoro-10,11-dihydro-9H-isoxazolo[4',5':5,6]pyrido[1,2,3-mn]phenoxazine-9,10-dione (I)

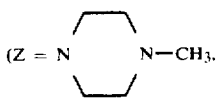

R=H).

EXAMPLE 2

6-(1-piperazinyl)-7-fluoro-10,11-dihydro-9H-isoxazolo[4',5':5,6]pyrido[1,2,3-mn]phenoxazine-9,10-dione (a) The procedure of Example 1 can be repeated, replacing the N-methylpiperazinyl in Example 1(g) with piperazine, to obtain 6-(1-piperazinyl)-7-fluoro-10,11-dihydro-9H-isoxazolo[4',5':5,6]pyrido[1,2,3-mn]phenoxazine-9,10-dione (I)

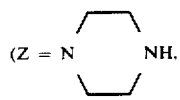

R=H).

(b) Alternatively, the title compound is prepared as follows: To a solution of 2.67 g of ethyl 2,3,4,5-tetrafluorobenzoyl acetate (A) ($R_{11}=C_2H_5$) in 30 ml of tetrahydrofuran (THF) is added 1.93 g of the isothiocyanate (B) (R=H). The solution is cooled with an ice bath, and 0.41 g of a 60% sodium hydride in-oil suspension is then added into the mixture. After 18 hours, 0.65 ml of methyl iodide is added. The reaction is allowed to react at room temperature for 16 hours. 1 ml of acetic acid is added into the mixture and the solution is removed by evaporation under reduced pressure. The residue is dissolved in methylene chloride (300 ml) and washed with saturated sodium chloride solution. The organic layer is dried and purified through a silica gel column to give 3.7 g of compound (C) (R=H, $R_{11}=C_2H_5$).

(c) 200 mg of 60% sodium hydride-in-oil suspension is added slowly to 2.7 g of the preceding compound (C) (R=H, $R_{11}=C_2H_5$) in 40 ml THF in 0° C. After the addition, the mixture is heated at 65° C. for 16 hours. After cooling, 0.5 ml of acetic acid is added and the solvent is removed by distillation under reduced pressure. The residue is dissolved in 250 ml methylene chloride and washed with saturated sodium chloride soltuion. The organic portion is dried and evaporated to dryness. A 50% mixture of hexane and ether is added into the residue and filtered, yielding the 1,4-dihydro-4-oxoquinoline-3-carboxylic acid ester (D) (R=H, $R_{11}=C_2H_5$).

(d) To a solution of 4.5 g of (D) R=H, $R_{11}=C_2H_5$) in 100 ml acetonitrile is added 10 ml 3N hydrochloric acid. The solution is heated at 50° C. for 3 hours. The solution is then removed by evporation under reduced pressure. Ether (50 ml) is added and filtered yielding 3.8 g of the phenol (E) (R=H, $R_{11}=C_2H_5$).

(e) 200 mg of 60% sodium hydride-in-oil suspension is added to a cold solution of 2.0 g of (E) (R=H, $R_{11}=C_2H_5$) in dry dimethylformamide. After the addition, the solution is heated at 100° C. under nitrogen atmosphere for 16 hours. It is then cooled and 0.5 ml of acetic acid is added. The solvent is then removed under reduced pressure. The residue is dissolved in 400 ml methylene chloride and washed with saturated sodium chloride solution. It is then dired and evaporated to dryness under reduced pessure. Ether (100 ml) is added and filtered yielding the phenoxazine derivative (F) (R=H, $R_{11}=C_2H_5$).

(f) To a solution of 3.8 g of (F) (R=H, $R_{11}=C_2H_5$) in pyridine (50 ml) is added 6 g of N-carbobenzoxypiperazine. The mixture is heated at 110° C. for 2 days. The solvent is removed by evaporation under reduced pressure. Ether is added in and filtered. The residue is then washed with water and then ether giving the residue (G) (R=H, $R_{11}=C_2H_5$), Z=4-carbobenzoxypiperazin-1-yl).

(g) To a solution of 1.47 g of (G) (R=H, $R_{11}=C_2H_5$) in 100 ml methylene chloride at room temperature is added 540 mg metachloroperbenzoic acid. After 1 day, 200 ml of methylene chloride is added and the solution is washed with cold dilute sodium bicarbonate solution. The organic layer is dried and evaporated to dryness. Crystallization from ethanol yields the sulfoxide (H) (R=H, $R_{11}=C_2H_5$).

(h) To a solution of 1.5 g of the sulfoxide (H) (R=H, $R_{11}=C_2H_5$) in 50 ml methanol is added 190 mg hydroxyurea and 380 mg DBU (1,8-diazabicyclo[5.4.0]undec-7-ene). After 1 day, the solution is removed and 2 ml of acetic acid and water (100 ml) are added. The mixture is filtered yielding (I)

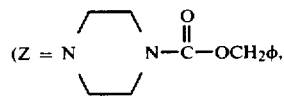

R=H).

(i) 1 g of the preceding compound (I) is dissolved in 5 ml of hydrogen bromide in glacial acetic acid. After 5 minutes, ether 150 ml is added and filtered and washed with ether again. It gives the title compound as the hydrobromide salt in good yield

EXAMPLE 3

6-(3-formamido-1-pyrrolidinyl)-7-fluoro-10,11-dihydro-9H-isoxazolo[4',5':5,6]pyrido[1,2,3-mn]phenoxazine-9,10-dione In the described fashion as Example 2(b)–2(h), replacing the N-carboxypiperazine in Example 2(f) with 3-formamido-1-pyrrolidine, one can obtain 6-(3-formamido-1-pyrrolidinyl)-7-fluoro-10,11-dihydro-9H-isoxazolo[4',5':5,6]pyrido[1,2,3-mn]phenoxazine-9,10-dione (I)

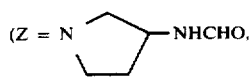

R=H).

EXAMPLE 4

6-(3-amino-1-pyrrolidinyl)-7-fluoro-10,11-dihydro-9H-isoxazolo[4',5':5,6]pyrido[1,2,3-mn]phenoxazine-9,10-dione The product of Example 3, I

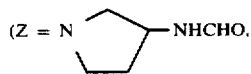

R=H) can be hydrolyzed by the use of dilute hydrochloric acid in acetonitrile to yield 6-(3-amino-1-pyrrolidinyl)-7-fluoro-10,11-dihydro-9H-isoxazolo[4',5':5,6]pyrido[1,2,3-mn]phenoxazine-9,10-dione hydrochloride salt (I)

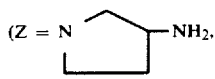

R=H).

EXAMPLE 5

3,7-difluoro-6-(4-methyl-1-piperazinyl)-10,11-dihydro-9H-isoxazolo[4',5':5,6]pyrido[1,2,3-mn]phenoxazine-9,10-dione (a) In the described fashion in Example 1(b) replacing methyl N-(2-fluorophenyl)iminochlorothioformate (4) (R=H) with methyl N-(2,4-difluorophenyl)iminochlorothioformate (4) (R=4-fluoro) one can obtain the 1,4-dihydro-4-oxo-quinoline-3-carboxylate (5) ($R_{11}$=$C_2H_5$, R=p—F).

(b) By following Example 1(c–f), the preceding compound (5) ($R_{11}$=$C_2H_5$, R=p—F) can yield the 3,6,7-trifluoro-10,11-dihydro-9H-isoxazolo[4',5':5,6-]pyrido[1,2,3-mn]phenoxazine-9,10-dione (9) (R=3—F).

(c) In the described fashion as Example 1(g) displacing the 6-fluoro with N-methylpiperazine, the preceding compound (9) can yield 3,7-difluoro-6-(4-methyl-1-piperazinyl)-10,11-dihydro-9H-isoxazolo[4',5':5,6-]pyrido[1,2,3-mn]phenoxazine-9,10-dione (I)

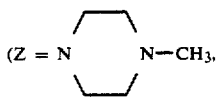

R=3—F).

EXAMPLE 6

By following the example 5(a–c), replacing the N-methylpiperazine in Example 5(c) with various amines such as piperazine, 3-formamidopyrrolidine, piperidine, pyrrolidine, morpholine, thiomorpholine, homopiperazine, N,N-dimethylhydrazine, 2-methylpiperazine, 2-phenylpiperazine, 2,6-dimethylpiperazine, 3-amino-4-methylpyrrolidine, 3-aminomethylpyrroldine, 3-aminomethyl-4-chloropyrrolidine, one can obtain the following compounds.

(a) 3,7-difluoro-6(1-piperazinyl)-10,11-dihydro-9H-isoxazolo[4',5':5,6]pyrido[1,2,3-mn]phenoxazine-9,10-dione (I)

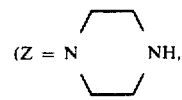

R=3—F).

(b) 3,7-difluoro-6-(3-formamido-1-pyrrolidinyl)-10,11-dihydro-9H-isoxazolo[4',5':5,6]pyrido[1,2,3-mn]phenoxazine-9,10-dione (I)

R=3-F).

(c) 3,7-difluoro-6-(1-piperidinyl)-10,11-dihydro-9H-isoxazolo[4',5':5,6]pyrido[1,2,3-mn]phenoxazine-9,10-dione (I)

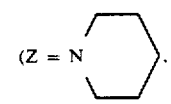

R=3—F).

(d) 3,7-difluoro-6-(1-pyrrolidinyl)-10,11-dihydro-9H-isoxazolo[4',5':5,6]pyrido[1,2,3-mn]phenoxazine-9,10-dione (I)

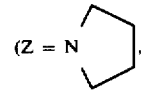

R=3—F).

(e) 3,7-difluoro-6-(1-morpholinyl)-10,11-dihydro-9H-isoxazolo[4',5':5,6]pyrido[1,2,3-mn]phenoxazine-9,10-dione (I)

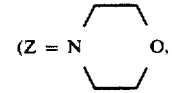

R=3—F).

(f) 3,7-difluoro-6-(1-thiomorpholinyl)-10,11-dihydro-9H-isoxazolo[4',5':5,6]pyrido[1,2,3-mn]phenoxazine-9,10-dione (I)

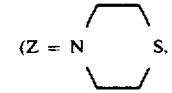

R=3—F).

(g) 3,7-difluoro-6-(1-homopiperazinyl)-10,11-dihydro-9H-isoxazolo[4',5':5,6]pyrido[1,2,3-mn]phenoxazine-9,10-dione (I)

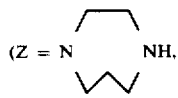

R=3—F).

(h) 3,7-difluoro-6-(1-N,N-dimethylhydrazyl)-10,11-dihydro-9H-isoxazolo[4',5':5,6]pyrido[1,2,3-mn]phenoxazine-9,10-dione (I) (Z=NH—N(CH3)2, R=3—F).

(i) 3,7-difluoro-6-(3-methyl-1,-piperazinyl)-10,11-dihydro-9H-isoxazolo[4',5':5,6]pyrido[1,2,3-mn]phenoxazine-9,10-dione (I)

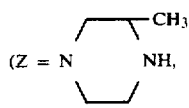

(j) 3,7-difluoro-6-(3-phenyl-1-piperazinyl)-10,11-dihydro-9H-isoxazolo[4',5':5,6]pyrido[1,2,3-mn]phenoxazine-9,10-dione (I)

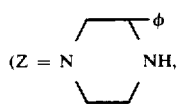

R=3—F).

(k) 3,7-difluoro-6-(3,4-dimethyl-1-piperazinyl)-10,11-dihydro-9H-isoxazolo[4',5':5,6]pyrido[1,2,3-mn]phenoxazine-9,10-dione (I)

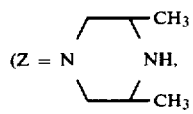

R=3—F).

(l) 3,7-difluoro-6-(3-amino-4-methyl-1-pyrrolidinyl)-10,11-dihydro-9H-isoxazolo[4',5':5,6]pyrido[1,2,3-mn]phenoxazine-9,10-dione (I)

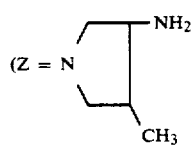

R=3—F).

(m) 3,7-difluoro-6-(3-aminomethyl-1-pyrrolidinyl)-10,11-dihydro-9H-isoxazolo[4',5':5,6]pyrido[1,2,3-mn]phenoxazine-9,10-dione (I)

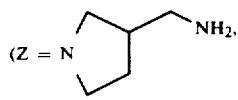

R=3—F).

(n) 3,7-difluoro-6-(3-aminomethyl-4-chloro-1-pyrrolidinyl)-10,11-dihydro-9H-isoxazolo[4',5':5,6-]pyrido[1,2,3-mn]phenoxazine-9,10-dione (I)

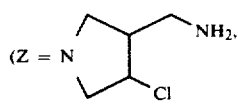

R=3—F).

EXAMPLE 7

3,7-difluoro-6-(3-amino-1-pyrrolidinyl)-10,11-difluoro-9H-isoxazolo-[4',5':5,6]pyrido[1,2,3-mn]phenoxazine-9,10-dione By following the procedure as Example (4), the product of Example 6(b) can be hydrolyzed to yield 3,7-difluoro-6-(3-amino-1-pyrrolidinyl)-10,11-dihydro-9H-isoxazolo[4',5':5,6]pyrido[1,2,3-mn]phenoxazine-9,10-dione hydrochloride salt (I)

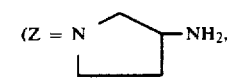

R=3—F).

EXAMPLE 8

1,3,7-trifluoro-6-(4-methyl-1-piperazinyl)-10,11-dihydro-9H-isoxazolo[4',5':5,6]pyrido[1,2,3-mn]phenoxazine-9,10-dione (a) In the described fashion as Example 1(b), replacing methyl N-(2-fluorophenyl)iminochlorothioformate (4) (R=H) with methyl N-(2,4,5-trifluorophenyl)iminochlorothioformate (4) (R=4-fluoro) one can obtain the 1,4-dihydro-4-oxo-quinoline-3-carboxylate (5) (R11=C2H5, R=o,p—di F).

(b) By following Example 1(c-f), the preceding compound (5) (R11=C2H5, R=o,p—di F) can yield the 1,3,6,7-tetrafluoro-10,11-dihydro-9H-isoxazolo[4',5'=5,6]pyrido[1,2,3-mn]phenoxazine-9,10-dione (9) (R=1,3—di F).

(c) In the described fashion as Example 1(g) displacing the 6-fluoro with N-methylpiperazine, the preceding compound (9) can yield 1,3,7-trifluoro-6-(4-methyl-1-piperazinyl)-10,11-dihydro-9H-isoxazolo[4',5':5,6-]pyrido[1,2,3-mn]phenoxazine-9,10-dione (I)

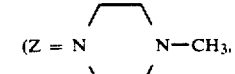

R=1,3—di F).

EXAMPLE 9

By following the Exanple (8)(a-c), replacing the N-methylpiperazine in Example (8)(c) with various amines such as piperazine, 3-formamidopyrrolidine, 3-((ethylamino)methyl)-pyrrolidine, one can obtain the following compounds.

(a) 1,3,7-trifluoro-6-(1-piperazinyl)-10,11-dihydro-9H-isoxazolo[4',5'-5,6]pyrido[1,2,3-mn]phenoxazine-9,10-dione (I)

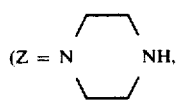

R = 1,3—di F).

(b) 1,3,7-6-(3-formamido-1-pyrrolidinyl)-10,11-dihydro-9H-isoxazolo[4',5':5,6]pyrido[1,2,3-mn]phenoxazine-9,10-dione (I)

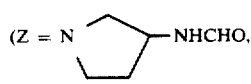

R = 1,3—di F).

(c) 1,3,7-trifluoro-6-(3-(ethylamino)methyl-1-pyrrolidinyl)-10,11-dihydro-9H-isoxazolo[4',5'-5,6]pyrido[1,2,3-mn]phenoxazine-9,10-dione (I)

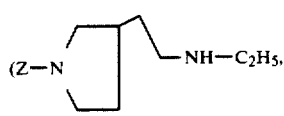

R = 1,3—di F).

EXAMPLE 10

1,3,7-trifluoro-6-(3-amino-1-pyrrolidinyl)-10,11-dihydro-9H-isoxazolo[4,',5':5,6]pyrido[1,2,3-mn]phenoxazine-9,10-dione By following the procedure as Example (4), the product of Example 9(b) can be hydrolyzed to yield 1,3,7-trifluoro-6-(3-amino-1-pyrrolidinyl)-10,11-dihydro-9H-isoxazolo[4',5':5,6]pyrido[1,2,3-mn]phenoxazine-9,10-dione hydrochloride salt (I)

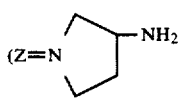

R = 1,3—di F).

EXAMPLE 11

In the described fashion as Example 1(b), replacing methyl N-(2-fluorophenyl)iminochlorothioformate (4) (R = H) with an appropriate N-substituted iminochloroformate (4) such as R equals to 4,5-methylenedioxy, 4-hydroxy, 4-methoxy, 4-methyl, one can obtain the following 1,4-dihydro-4-oxo-quinoline-3-carboxylate (5)

(a) Compound (5) R = m,p-methylenedioxy
(b) Compound (5) R = 4-hydroxy
(c) Compound (5) R = 4-methoxy
(d) Compound (5) R = 4-methyl

EXAMPLE 12

By following Example 1(c-f), the preceding compound (5)(a), (b), (c) and (d) can yield the following compounds:

(a) 2,3-methylenedioxy-6,7-difluoro-10,11-dihydro-9H-isoxazolo[4',5':5,6]pyrido[1,2,3-mn]phenoxazine-9,10-dione (9) (R = 2,3-methylenedioxy).

(b) 3-hydroxy-6,7-difluoro-10,11-dihydro-9H-isoxazolo[4',5':5,6]pyrido[1,2,3-mn]phenoxazine-9,10-dione (9) (R = 3—OH).

(c) 3-methoxy-6,7-difluoro-10,11-dihydro-9H-isoxazolo[4',5':5,6]pyrido[1,2,3-mn]phenoxazine-9,10-dione (9) R = 3—OCH₃).

(d) 3-methyl-6,7-difluoro-10,11-dihydro-9H-isoxazolo[4',5':5,6]pyrido-[1,2,3-mn]phenoxazine-9,10-dione (9) (R = 3—CH₃).

EXAMPLE 13

In the described fashion as Example 1(g), using compounds in Example 11(a-d) instead of compound (9) (R = H) and replacing N-methylpiperazine with an appropriate amine such as 3-methylaminopyrrolidine, 3-hydroxypyrrolidine, 3-hydroxymethylpyrrolidine, M-methylhydrazine, 1,2-diaminoethane, ethanolamine, ethylamine and 2-p-fluorophenylpiperazine, one can obtain the following compounds.

(a) 2,3-methylenedioxy-6-(3-methylamino-1-pyrrolidinyl)-7-fluoro-10,11-dihydro-9H-isoxazolo[4',5':5,6]pyrido[1,2,3-mn]phenoxazine-9,10-dione (I)

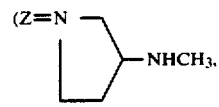

R = 2,3-methylenedioxy.)

(b) 3-hydroxy-6-(3-hydroxy-1-pyrrolidinyl)-7-fluoro-10,11-dihydro-9H-isoxazolo[4',5':5,6]pyrido[1,2,3-mn]phenoxazine-9,10-dione (I)

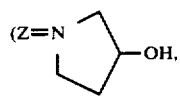

R = 3—OH).

(c) 3-methoxy-6-(3-hydroxymethyl-1-pyrrolidinyl)-7-fluoro-10,11-dihydro-9H-isoxazolo[4',5':5,6-]pyrido[1,2,3-mn]phenoxazine-9,10-dione (I)

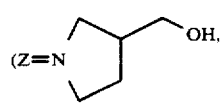

R = 3—OCH₃).

(d) 3-methyl-6-(2-methyl-1-hydrazyl)-7-fluoro-10,11-dihydro-9H-isoxazolo[4',5':5,6]pyrido[1,2,3-mn]phenoxazine-9,10-dione (I) (Z=NHNHCH₃, R=3-CH₃).

(e) 3-methyl-6-aminoethylamino-7-fluoro-10,11-dihydro-9H-isoxazolo[4',5':5,6]pyrido[1,2,3-mn]phenoxazine-9,10-dione (I) (Z=NHC₂H₄NH₂, R=3—CH₃).

(f) 3-methyl-6-hydroxyethylamino-7-fluoro-10,11-dihydro-9H-isoxazolo[4',5':5,6]pyrido[1,2,3-mn]phenoxazine-9,10-dione (I) (Z=NHC₂H₄OH, R=3—CH₃).

(g) 3-methyl-6-ethylamino-7-fluoro-10,11-dihydro-9H-isoxazolo[4',5':5,6]pyrido[1,2,3-mn]phenoxazine-9,10-dione (I) (Z=NHC₂H₅, R=3—CH₃).

(h) 3-methyl-6-(3-p-fluorophenyl-1-piperazinyl)-7-fluoro-10,11-dihydro-9H-isoxazolo[4',5':5,6-]pyrido[1,2,3-mn]phenoxazine-9,10-dione (I)

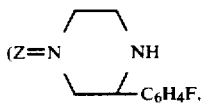

R=3—CH₃).

EXAMPLE 14

6-(3-N-ethylaminomethylpyrrolidin-1-yl)-7-fluoro-10,11-dihydro-9H-isoxazolo[4',5':5,6]pyrido[1,2,3-mn]phenoxazine-9,10-dione In the described fashion as Example 2(b)–2(h), replacing the N-carbobenzoxypiperazine in Example 2(f) with 3-(N-carbobenzoxy-N-ethyl aminomethyl)pyrrolidine, one can obtain 6-(3-N-ethylaminomethylpyrrolidin-1-yl)-7-fluoro-10,11-dihydro-9H-isoxazolo[4',5':5,6-]pyrido[1,2,3-mn]phenoxazine-9,10-dione (I) (R=H,

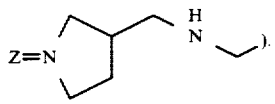

EXAMPLE 15

6-(4-methyl-1-piperazinyl)-7-fluoro-10,11-dihydro-9H-isothiazolo[4',5':5,6]pyrido[1,2,3-mn]phenoxazine-9,10-dione (a) A mixture of 1.17 g of 2,4,5-trifluoro-3-acetyloxybenzoic acid (1') and thionyl chloride (10 ml) and 1 drop of dimethylformamide is heated at refluxing temperature for 4 hours. The solution is evaporated to dryness to give the acid chloride (2'). This acid chloride, dissolved in 10 ml of tetrahydrofuran (THF) is added slowly to a solution of 1.32 g of ethylmalonate monoester in 25 ml of THF solution containing 9.09 ml of 2.2 molar solution of n-butyl lithium in hexane at −60° C. It is allowed to stir at −55° C. to −60° C. for 1 hour. The solution is allowed to warm up to room temperature and then acidified with 20 ml of 1N hydrochloric acid and extracted with ether. The ether extract is washed with saturated NaHCO₃ and then water, and dried to yield 1.29 g of the ketoester (3) (R₁₁=C₂H₅).

(b) 800 mg of a 60% sodium hydride-in-oil suspension is slowly added to a solution of 2.03 g methyl N-(2-fluorophenyl)iminochlorothioformate (4') (R=H) and 4.34 g ketoester (3') (R₁₁=C₂H₅). The mixture is then heated at reflux for 24 hours. It is then cooled and evaporated under reduced pressure to dryness. The residue is dissolved in methylene chloride and washed with saturated sodium chloride solution. Organic layer is separated and dried over magnesium sulfate. The product is purified through silica gel column yielding the 1,4-dihydro-4-oxo-quinoline-3-carboxylate (5') (R₁₁=C₂H₅, R=H).

(c) To a solution of 2.75 g of the preceding compound (5') (R₁₁=C₂H₅, R=H) in 30 ml acetonitrile is added in 10 ml 2N hydrochloric acid solution. The mixture is stirred for 24 hours at room temperature. The mixture is then evaporated to dryness and redissolved in THF. 200 mg of sodium hydride is added. After heating for 24 hours at 50° C. the reaction mixture is then evaporated under reduced pressure to dryness. The residue is dissolved in methylene chloride and washed with water. The organic solvent is separated and dried and evaporated to dryness. After purification, it yields the phenoxazine derivative (6') (R₁₁=C₂H₅, R=H).

(d) To a solution of 3.90 g of the preceding compound (6') (R₁₁=C₂H₅, R=H) in 100 ml methylene chloride is added in 2.18 g of 80% metachloroperbenzoic acid. After stirring at 25° C. for 2 days, the solution is diluted with 150 ml of methylene chloride and washed with dilute sodium bicarbonate solution. The organic solvent is dried over magnesium and evaporated to dryness. 15 ml of ether is added to the residue and it crystallizes yielding, after filtration the sulfoxide (7') (R₁₁=C₂H₅, R=H).

(e) 2.18 ml of 0.92N sodium hydrosulfide solution is added to 820 mg of the preceding sulfoxide (7') (R₁₁=C₂H₅, R=H) in 10 ml THF. After the solution is stirred at room temperature, the solution is diluted with 30 ml water containing 252 mg NaHCO₃ and extracted with ether twice. The aqueous solution is cooled to 5° C. and acidified with 6 ml 1N hydrochloric acid. The precipitate is filtered and dried yielding the mercaptophenoxazine derivative (8') (R₁₁=C₂H₅, R=H).

(f) To a solution of 375 mg of the preceding compound (8') (R₁₁=C₂H₅, R=H) in 8 ml of THF and 20 ml of water solution containing 1.8 g sodium bicarbonate is added in 450 mg hydroxylamine —O— sulfonic acid. After stirring for 4 hours, the mixture is diluted with water (20 ml) and is extracted with ether (25 ml×2). The aqueous portion is acidified to pH 3 and the precipitate is filtered yielding 6,7-difluoro-10,11-9H-isothioazolo[4',5':5,6]pyrido[1,2,3-mn]phenoxazine-9,10-dione (9') (R=H).

(g) To a solution of 1.67 g of the preceding isothiazolo-pyrido-phenoxazine derivative (9') (R=H) in 30 ml pyridine is added in 2.5 ml N-methylpiperazine. It is then heated under Nitrogen atmosphere at 60° C. for 24 hours. The mixture is evaporated to dryness and is then boiled in ethanol for 5 minutes and the mixture is filtered and washed with water yielding the 6-(4-methyl-1-piperazinyl)-7-fluoro-10,11-dihydro-9H-isothiazo[4',5':5,6]pyrido[1,2,3-mn]phenoxazine-9,10-dione (I')

R=H).

EXAMPLE 16

6(1-piperazinyl)-7-fluoro-10,11-dihydro-9H-isothiazolo[4',5':5,6]pyrido[1,2,3-mn]phenoxazine-9,10-dione (a) The procedure of Example 15 can be repeated, replacing the N-methylpiperazinyl in Example 15(g) with piperazine, to obtain 6-(1-piperazinyl)-7-fluoro-10,11-dihydro-9H-isothiazolo[4',5':5,6]pyrido[1,2,3-mn]phenoxazine-9,10-dione (I')

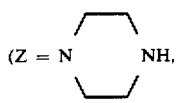

R=H).

(b) Alternatively, the title compound is prepared as follows: To a solution of 2.94 g of (G) (R=H, $R_{11}=C_2H_5$), product example 2(f) in 30 ml THF is added 850 mg of sodium hydrosulfide in 2 ml of water. The mixture is stirred at 35° C. for 10 hours. The solvent is removed by reduced pressure and the residue is dissolved in water (200 ml). Acetic acid is added until the pH of the solution is 6. The precipitate is filtered and washed with water and ether yielding (J) in good yield (R=H, $R_{11}=C_2H_5$).

(c) To a solution of 1.15 g (J) (R=H, $R_{11}=C_2H_5$) in 25 ml THF and 15 ml water solution containing 1 g of sodium bicarbonate is added 800 mg hydroxylamine-O-sulfonic acid. After stirring for 1 day, the precipitate is filtered yielding (I)

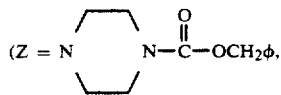

R=H).

(d) 1 g of the preceding compound is dissolved in 5 ml of hydrogen bromide in glacial acetic acid. After 5 minutes, ether (150 ml) is added and the residue is filtered and washed with ether yielding the title compound as the hydrobromide salt in good yield.

EXAMPLE 17

6-(3-formamido-1-pyrrolidinyl)-7-fluoro-10,11-dihydro-9H-isothiazolo[4', 5':5,6]pyrido[1,2,3-mn]phenoxazine-9,10-dione In the described fashion as Example 15, replacing the N-methylpiperazine in Example 15(g) with 3-formamido-pyrrolidine, one can obtain 6-(3-formamido-1-pyrrolidinyl)-7-fluoro-10,11-dihydro-9H-isothiazolo[4',5':5,6]pyrido[1,2,3-mn]phenoxazine-9,10-dione (I')

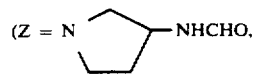

R=H).

EXAMPLE 18

6-(3-amino-1-pyrrolidinyl)-7-fluoro-10,11-dihydro-9H-isothiazolo[4',5':5,6]pyrido[1,2,3-mn]phenoxazine-9,10-dione The product of Example 17, I

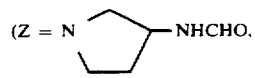

R=H) can be hydrolyzed by the use of dilute hydrochloric acid in acetonitrile to yield 6-(3-amino-1-pyrrolidinyl)-7-fluoro-10,11-dihydro-9H-isothiazolo[4',5':5,6]pyrido[1,2,3-mn]phenoxazine-9,10-dione hydrochloride salt (I')

R=H).

EXAMPLE 19

3,7-difluoro-6-(4-methyl-1-piperazinyl)-10,11-dihydro-9H-isothiazolo[4',5':5,6]pyrido[1,2,3-mn]phenoxazine-9,10-dione (a) In the described fashion in Example 15(b) replacing methyl N-(2-fluorophenyl)iminochlorothioformate (4') (R=H) with methyl N-(2,4-difluorophenyl)iminochlorothioformate (4') (R=4-fluoro) one can obtain the 1,4-dihydro-4-oxo-quinoline-3-carboxylate (5') ($R_{11}=C_2H_5$, R=p—F).

(b) By following Example 15(c-f), the preceding compound (5') ($R_{11}=C_2H_5$, R=p—F) can yield the 3,6,7-trifluoro-10, 11-dihydro-9H-isothiazolo[4',5':5,6-]pyrido[1,2,3-mn]phenoxazine-9,10-dione (9') (R=3—F).

(c) In the described fashion as Example 15(g) displacing the 6-fluoro with N-methylpiperazine, the preceding compound (9') can yield 3,7-difluoro-6-(4-methyl-1-piperazinyl)-10,11-dihydro-9H-isothiazolo[4',5':5,6-]pyrido[1,2,3-mn]phenoxazine-9,10-dione (I')

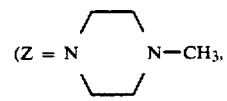

R=3—F).

EXAMPLE 20

By following the example 19(a-c), replacing the N-methylpiperazine in Example 19(c) with various amines such as piperazine, 3-formamidopyrrolidine, piperidine, pyrrolidine, morpholine, thiomorpholine, homopiperazine, N,N-dimethylhydrazine, 2-methylpiperazine, 2-phenylpiperazine, 2,6-dimethylpiperazine, 3-amino-4-methylpyrrolidinyl, 3-aminomethylpyrrolidine, 3-aminomethyl-4-chloro-1-pyrrolidine one can obtain the following compounds.

(a) 3,7-difluoro-6-(1-piperazinyl)-10,11-dihydro-9H-isothiazolo[4′,5′:5,6]pyrido[1,2,3-mn]phenoxazine-9,10-dione (I′)

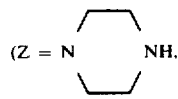

R=3—F).

(b) 3,7-difluoro-6-(3-formamido-1-pyrrolidinyl)-10,11-dihydro-9H-isothiazolo[4′,5′:5,6]pyrido[1,2,3-mn]phenoxazine-9,10-dione (I′)

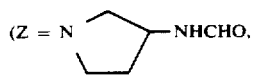

R=3—F).

(c) 3,7-difluoro-6-(1-piperidinyl)-10,11-dihydro-9H-isothiazolo[4′,5′:5,6]pyrido[1,2,3-mn]phenoxazine-9,10-dione (I′)

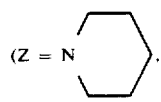

R=3—F).

(d) 3,7difluoro-6(1-pyrrolidinyl)-10,11-dihydro-9H-isothiazolo[4′,5′:5,6]pyrido[1,2,3-mn]phenoxazine-9,10dione (I′)

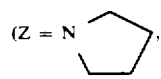

R=3—F).

(e) 3,7-difluoro-6-(1-morpholinyl)-10,11-dihydro-9H-isothiazolo[4′,5′:5,6]pyrido[1,2,3-mn]phenoxazine-9,10-dione (I′)

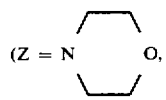

R=3—F).

(f) 3,7-difluoro-6-(1-thiomorpholinyl)-10,11-dihydro-9H-isothiazolo[4′,5′:5,6]pyrido[1,2,3-mn]phenoxazine-9,10-dione (I′)

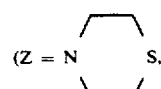

R=3—F).

(g) 3,7-difluoro-6-(1-homopiperazinyl)-10,11-dihydro-9H-isothiazolo[4′:5′5,6]pyrido[1,2,3-mn]phenoxazine-9,10dione (I′)

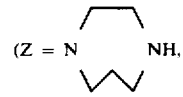

R=3—F).

(h) 3,7-difluoro-6-(1-N,N-dimethylhydrazyl)-10,11-dihydro-9H-isothiazolo[4′,5′:5,6]pyrido[1,2,3-mn]phenoxazine-9,10-dione (I′) (Z=NH—N(CH$_3$)$_2$, R=3—F).

(i) 3,7-difluoro-6-(3-methyl-1-piperazinyl)-10,11-dihydro-9H-isothiazolo[4′,5′:5,6]pyrido[1,2,3-mn]phenoxazine-9,10-dione (I′)

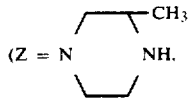

R=3—F).

(j) 3,7-difluoro-6-(3-phenyl-1-piperazinyl)-10,11-dihydro-9H-isothiazolo[4′,5′:5,6]pyrido[1,2,3-mn]phenoxazine-9,10-dione (I′)

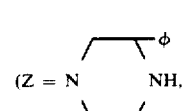

R=3—F).

(k) 3,7-difluoro-6-(3,5-dimethyl-1-piperazinyl)-10,11-dihydro-9H-isothiazolo[4′,5′:5,6]pyrido[1,2,3-mn]phenoxazine-9,10-dione (I′)

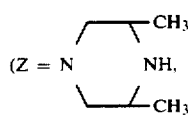

R=3—F).

(l) 3,7-difluoro-6-(3-amino-4-methyl-1-pyrrolidinyl)-10,11-dihydro-9H-isothiazolo[4′,5′:5,6]pyrido[1,2,3-mn]phenoxazine-9,10-dione (I′)

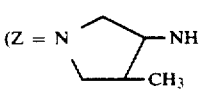

R=3—F).

(m) 3,7-difluoro-6-(3-aminomethyl-1-pyrrolidinyl)-10,11-dihydro-9H-isothiazolo[4′,5′:5,6]pyrido[1,2,3-mn]phenoxazine-9,10-dione (I′)

R=3—F).

(n) 3,7-difluoro-6-(3-aminomethyl-4-chloro-1-pyrrolidinyl)-10,11-dihydro-9H-isothiazolo[4',5':5,6-]pyrido[1,2,3-mn]phenoxazine-9,10-dione (I')

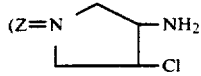

R=3—F).

EXAMPLE 21

3,7-difluoro-6-(3-amino-1-pyrrolidinyl)-10,11-difluoro-9H-isothiazolo-[4',5':5,6]pyrido[1,2,3-mn]phenoxazine-9,10-dione By following the procedure as Example (18), the product of Example 20(b) can be hydrolyzed to yield 3,7-difluoro-6-(3-amino-1-pyrrolidinyl)-10,11-dihydro-9H-isothiazolo[4',5':5,6]pyrido[1,2,3-mn]phenoxazine-9,10-dione hydrochloride salt (I')

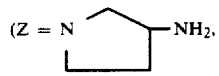

R=3—F).

EXAMPLE 22

1,3,7-trifluoro-6-(4-methyl-1-piperazinyl)-10,11-dihydro-9H-isothiazolo[4',5':5,6]pyrido[1,2,3-mn]phenoxazine-9,10-dione (a) In the described fashion as Example 15(b), replacing methyl N-(2-fluorophenyl)iminochlorothioformate (4') (R=H) with methyl N-(2,4,5-trifluorophenyl)iminochlorothioformate (4') (R=4—fluoro) one can obtain the 1,4-dihydro-4-oxo-quinoline-3-carboxylate (5') ($R_{11}$=C$_2$H$_5$, R=o,p—di F).

(b) By following Example 15(c-f), the preceding compound (5') ($R_{11}$=C$_2$H$_5$, R=o,p—di F) can yield the 1,3,6,7-tetrafluoro-10,11-dihydro-9H-isothiazolo[4',5'-5,6]pyrido[1,2,3-mn]phenoxazine-9,10-dione (9') (R=1,3—di F).

(c) In the described fashion as Example 15(g) displacing the 6-fluoro with N-methylpiperazine, the preceding compound (9') can yield 1,3,7-trifluoro-6-(4-methyl-1-piperazinyl)-10,11-dihydro-9H-isothiazolo[4',5'-5,6]pyrido[1,2,3-mn]phenoxazine-9,10-dione (I')

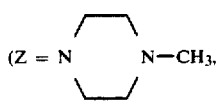

R=1,3—di F).

EXAMPLE 23

By following the Example 22(a-c), replacing the N-methylpiperazine in Example 22(c) with various amines such as piperazine, 3-formamidopyrrolidine, 3-((ethylamino)methyl)-pyrrolidine, one can obtain the following compounds.

(a) 1,3,7-trifluoro-6-(1-piperazinyl)-10,11dihydro-9H-isothiazolo[4',5'-5,6]pyrido[1,2,3-mn]phenoxazine-9,10-dione (I')

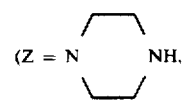

R=1,3—di F).

(b) 1,3,7-6-(3-formamido-1-pyrrolidinyl)-10,11-dihydro-9H-isothiazolo[4',5':5,6]pyrido[1,2,3-mn]phenoxazine-9,10-dione (I')

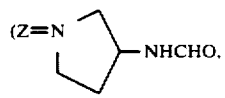

R=1,3—di F).

(c) 1,3,7-trifluoro-6-(3-(ethylamino)methyl-1-pyrrolidinyl)-10,11-dihydro-9H-isothiazolo[4',5'-5,6]pyrido[1,2,3-mn]phenoxazine-9,10-dione (I')

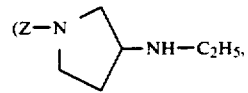

R=1,3—di F).

EXAMPLE 24

1,3,7-trifluoro-6-(3-amino-1-pyrrolidinyl)-10,11-dihydro-9H-isothiazolo[4',5':5,6]pyrido[1,2,3-mn]phenoxazine-9,10dione By following the procedure as Example (18), the product of Example 23(b) can be hydrolyzed to yield 1,3,7-trifluoro-6-(3-amino-1-pyrrolidinyl)-10,11-dihydro-9H-isothiazolo[4',5':5,6]pyrido[1,2,3-mn]phenoxazine-9,10-dione hydrochloride salt (I')

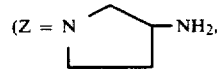

R=1,3—di F).

EXAMPLE 25

In the described fashion as Example 15(b), replacing methyl N-(2-fluorophenyl)iminochlorothioformate (4') (R=H) with an appropriate N-substituted iminochloroformate (4') such as R equals to 4,5-methylenedioxy, 4-hydroxy, 4-methoxy, or 4-methyl one can obtain the following 1,4-dihydro-4-oxo-quinoline-3-carboxylate (5')(a), (b), (c) and (d)

(a) Compound (5') R=m,p-methylenedioxy
(b) Compound (5') R=4-hydroxy
(c) Compound (5') R=4-methoxy
(d) Compound (5') R=4-methyl

EXAMPLE 26

By following Example 15(c–f), the preceding compound (5')(a), (b), (c) and (d) can yield the following compounds:

(a) 2,3-methylenedioxy-6,7-difluoro-10,11-dihydro-9H-isothiazolo[4',5':5,6]pyrido[1,2,3-mn]phenoxazine-9,10-dione (9') (R=2,3-methylenedioxy).

(b) 3-hydroxy-6,7-difluoro-10,11-dihydro-9H-isothiazolo[4',5':5,6]pyrido[1,2,3-mn]phenoxazine-9,10-dione (9') (R=3—OH).

(c) 3-methoxy-6,7-difluoro-10,11-dihydro-9H-isothiazolo[4',5':5,6]pyrido[1,2,3-mn]phenoxazine-9,10-dione (9') (R=3—OCH$_3$).

(d) 3-methyl-6,7-difluoro-10,11-dihydro-9H-isothiazolo[4',5':5,6]pyrido-[1,2,3-mn]phenoxazine-9,10-dione (9') (R=3—CH$_3$).

EXAMPLE 27

In the described fashion as Example 15(g), using compounds in Example 25(a–d) instead of compound (9') (R=H) and replacing N-methylpiperazine with an appropriate amine such as 3-methylamino-pyrrolidine, 3-hydroxypyrrolidine, 3-hydroxymethylpyrrolidine, N-methylhydrazine, 1,2-diaminoethane, ethanolamine, ethylamine and 2-p-fluorophenylpiperazine, one can obtain the following compounds.

(a) 2,3-methylenedioxy-6-(3-methylamino-1-pyrrolidinyl)-7-fluoro-10,11-dihydro-9H-isothiazolo[4',5':5,6]pyrido[1,2,3-mn]phenoxazine-9,10-dione (I')

(Z=N⟩—NHCH$_3$.

R=2,3-methylenedioxy.)

(b) 3-hydroxy-6-(3-hydroxy-1-pyrrolidinyl)-7-fluoro-10,11-dihydro-9H-isothiazolo[4',5':5,6]pyrido[1,2,3-mn]phenoxazine-9,10-dione (I')

(Z=N⟩—OH.

R=3—OH).

(c) 3-methoxy-6-(3-hydroxymethyl-1-pyrrolidinyl)-7-fluoro-10,11-dihydro-9H-isothiazolo[4',5':5,6-]pyrido[1,2,3-mn]phenoxazine-9,10-dione (I')

(Z=N⟩—OH.

R=3—OCH$_3$).

(d) 3-methyl-6-(2-methyl-1-hydrazyl)-7-fluoro-10,11-dihydro-9H-isothiazolo[4',5':5,6]pyrido[1,2,3-mn]phenoxazine-9,10-dione (I') (Z=NHNHCH$_3$, R=3—CH$_3$).

(e) 3-methyl-6-aminoethylamino-7-fluoro-10,11-dihydro-9H-isothiazolo[4',5':5,6]pyrido[1,2,3-mn]phenoxazine-9,10-dione (I') (Z=NHC$_2$H$_4$NH$_2$, R=3—CH$_3$).

(f) 3-methyl-6-hydroxyethylamino-7-fluoro-10,11-dihydro-9H-isothiazolo[4',5':5,6]pyrido[1,2,3-mn]phenoxazine-9,10-dione (I') (Z=NHC$_2$H$_4$OH, R=3—CH$_3$).

(g) 3-methyl-6-ethylamino-7-fluoro-10,11-dihydro-9H-isothiazolo[4',5':5,6]pyrido[1,2,3-mn]phenoxazine-9,10-dione (I') (Z=NHC$_2$H$_5$, R=3—CH$_3$).

(h) 3-methyl-6-(3-p-fluorophenyl-1-piperazinyl)-7-fluoro-10,11-dihydro-9H-isothiazolo[4',5':5,6-]pyrido[1,2,3-mn]phenoxazine-9,10-dione (I')

(Z=N⟩N—NH⟩—C$_6$H$_4$F,

R=3—CH$_3$).

It will be understood that various changes and modifications can be made in the details of procedure, formulation and use without departing from the spirit of the invention, especially as defined in the following claims.

What is claimed is:

1. A compound having the formula wherein B is selected from oxygen and sulfur; and R is one or more of hydrogen, halogen, C$_1$ to C$_4$ alkyl, a methylenedioxy group, a hydroxy and a alkoxy groups and Z is selected from an amino group of the formula $$-N\begin{matrix}R_4\\R_5\end{matrix}$$

wherein R$_4$ is hydrogen, C$_1$ to C$_4$ alkyl, amino-substituted C$_1$ to C$_4$ alkyl, hydroxy-substituted C$_1$ to C$_4$ alkyl, and R$_5$ is selected from the group consisting of C$_1$ to C$_4$ alkyl, hydroxy-substituted C$_1$ to C$_4$ alkyl, an amino group, a mono-(C$_1$ to C$_4$) alkylamino group and a di-(C$_1$ to C$_4$) alkylamino group; and an aliphatic heterocyclic ring having the structure wherein $R_6$ is a group of formula —(CH)— wherein n is 2 or 3 or a group of the formula or —(CH$_2$)—R$_7$—CH$_2$— wherein n is 1 or 2 and $R_7$ is selected from the group consisting of —S—, —O— and —NH—; substituted derivatives of the aliphatic heterocyclic ring substituted with one or more substituents selected from the group consisting of $C_1$ to $C_4$ alkyl, hydroxy-substituted $C_1$ to $C_4$ alkyl, hydroxy, halogen, phenyl, halophenyl, amino-substituted $C_1$ to $C_4$ alkyl, alkanoylamido containing 1 to 4 carbon atoms and an amino of the formula

wherein $R_8$ and $R_9$ are each independently selected from the group consisting of hydrogen, $C_1$ to $C_4$ alkyl; and pharmaceutically acceptable salts thereof.

2. A compound as defined in claim 1 wherein Z is selected from the group consisting of piperazinyl groups, piperidinyl groups, pyrrolidinyl groups, morpholino groups, thiomorpholino groups and homopiperazinyl groups and substituted derivatives thereof.

3. A compound as defined in claim 1 wherein B is oxygen.

4. A compound defined in claim 3 wherein R is a fluoro; and Z is piperazinyl, 4-methyl-1-piperazinyl, 3-amino-1-pyrrolidinyl, 3-methyl-1piperazinyl, 3-amino-4-methylpyrrolidinyl, 3-aminomethyl-4-chloro-1-pyrrolidinyl, or 3-(N-ethyl aminomethyl)pyrrolidinyl.

5. A compound defined in claim 3 wherein R is hydrogen; and Z is piperazinyl, 4-methyl-1-piperazinyl, 3-amino-1pyrrolidinyl, or 3-methyl-1-piperazinyl.

6. A compound defined in claim 3 wherein R is difluoro; and Z is piperazinyl, 4-methyl-1-piperazinyl or 3-amino-1-pyrrolidinyl.

7. A compound as recited in claim 1 wherein B is sulfur.

8. A compound defined in claim 7 wherein R is a fluoro; and Z is piperazinyl, 4-methyl-1-piperazinyl, 3-amino-1-pyrrolidinyl, 3-methyl-1-piperazinyl, 3-amino-4methyl-1-pyrrolidinyl, 3-aminomethyl-4-chlor-1-pyrrolidinyl, or 3(N-ethyl aminoethyl)-1-pyrrolidinyl.

9. A compound defined in claim 7 wherein R is hydrogen; and Z is piperazinyl, 4-methyl-1piperazinyl or 3-amino-1-pyrrolidinyl.

10. A compound defined in claim 7 wherein R is difluoro; and Z is piperazinyl, 4-methyl-1piperazinyl, 3-methyl-1-piperazinyl, or 3-amino-1-pyrrolidinyl.

11. A composition having antibacterial activity in pharmaceutical dosage form containing a diluent and a compound as defined in claim 1.

12. A method of treating a bacterial infection in a patient comprising administering to a patient in need of such treatment a therapeutically effective amount of a compound as defined in claim 1.

* * * * *

UNITED STATES PATENT AND TRADEMARK OFFICE
CERTIFICATE OF CORRECTION

PATENT NO. : 4,689,325
DATED : August 25, 1987
INVENTOR(S) : Daniel T. Chu

It is certified that error appears in the above—identified patent and that said Letters Patent is hereby corrected as shown below:

Column 33, line 34 should read:

3-amino-1-pyrrolidinyl, 3-methyl-1-piperazinyl, 3-

Column 34, line 6 should read:

3-amino-1-pyrrolidinyl, or 3-methyl-1-piperazinyl.

Column 34, line 16 should read:

amino-4-methyl-1-pyrrolidinyl, 3-aminomethyl-4-chloro-

Column 34, line 20 should read:

drogen; and Z is piperazinyl, 4-methyl-1-piperazinyl or

Column 32, line 62, the structure should be as follows:

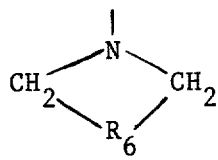

Signed and Sealed this

Fifth Day of July, 1988

Attest:

DONALD J. QUIGG

Attesting Officer      Commissioner of Patents and Trademarks